United States Patent
Han et al.

(10) Patent No.: US 10,518,233 B2
(45) Date of Patent: Dec. 31, 2019

(54) PHYTASE FORMULATION

(71) Applicant: BASF ENZYMES LLC, San Diego, CA (US)

(72) Inventors: Yun Han, San Diego, CA (US); Michael Pratt, San Diego, CA (US); Yi Wu, San Diego, CA (US)

(73) Assignee: BASF Enzymes LLC, San Diego, CA (US)

( * ) Notice: Subject to any disclaimer, the term of this patent is extended or adjusted under 35 U.S.C. 154(b) by 0 days.

(21) Appl. No.: 14/770,766

(22) PCT Filed: Mar. 10, 2014

(86) PCT No.: PCT/US2014/022433
§ 371 (c)(1),
(2) Date: Aug. 26, 2015

(87) PCT Pub. No.: WO2014/159185
PCT Pub. Date: Oct. 2, 2014

(65) Prior Publication Data
US 2016/0007633 A1   Jan. 14, 2016

Related U.S. Application Data

(60) Provisional application No. 61/784,947, filed on Mar. 14, 2013.

(30) Foreign Application Priority Data

May 16, 2013  (GB) .................................. 1308843.0

(51) Int. Cl.
*B01J 2/16* (2006.01)
*C12N 9/16* (2006.01)

(52) U.S. Cl.
CPC ................ *B01J 2/16* (2013.01); *C12N 9/16* (2013.01); *C12Y 301/03008* (2013.01); *C12Y 301/03026* (2013.01); *C12Y 301/03072* (2013.01)

(58) Field of Classification Search
CPC ...... B01J 2/16; C12N 9/16; C12Y 301/03008; C12Y 301/03026; C12Y 301/03072
USPC ....................................................... 424/94.3
See application file for complete search history.

(56) References Cited

U.S. PATENT DOCUMENTS

| | | |
|---|---|---|
| 4,179,522 A | 12/1979 | Huitson |
| 5,605,793 A | 2/1997 | Stemmer |
| 5,707,843 A | 1/1998 | Monte |
| 5,811,238 A | 9/1998 | Stemmer et al. |
| 5,824,514 A | 10/1998 | Kauffman et al. |
| 5,830,696 A | 11/1998 | Short |
| 5,830,721 A | 11/1998 | Stemmer et al. |
| 5,955,358 A | 9/1999 | Huse |
| 5,965,408 A | 10/1999 | Short |
| 6,171,820 B1 | 1/2001 | Short |
| 6,238,884 B1 | 5/2001 | Short et al. |
| 6,287,861 B1 | 9/2001 | Stemmer et al. |
| 6,287,862 B1 | 9/2001 | Delcardayre et al. |
| 6,291,242 B1 | 9/2001 | Stemmer et al. |
| 6,309,872 B1 | 10/2001 | Rey et al. |
| 6,335,179 B1 | 1/2002 | Short et al. |
| 6,352,842 B1 | 3/2002 | Short et al. |
| 6,358,709 B1 | 3/2002 | Short et al. |
| 6,361,974 B1 | 3/2002 | Short et al. |
| 6,440,668 B1 | 8/2002 | Short |
| 6,537,776 B1 | 3/2003 | Short |
| 6,764,835 B2 | 7/2004 | Short |
| 8,334,124 B1 | 12/2012 | Mullaney et al. |
| 8,361,956 B2 | 1/2013 | Malboobi et al. |
| 8,877,478 B2 | 11/2014 | Steer et al. |
| 2003/0054511 A1 | 3/2003 | Andela et al. |
| 2005/0130160 A1 | 6/2005 | Chew et al. |
| 2005/0186666 A1 | 8/2005 | Schneider et al. |
| 2007/0196449 A1 | 8/2007 | Lei |
| 2008/0058262 A1 | 3/2008 | Rasochova et al. |
| 2008/0090276 A1 | 4/2008 | Van Dyck et al. |
| 2009/0074909 A1 | 3/2009 | Webel et al. |
| 2009/0263543 A1 | 10/2009 | Lohscheidt et al. |
| 2009/0274795 A1 | 11/2009 | Lohscheidt et al. |
| 2010/0124586 A1 | 5/2010 | Becker et al. |
| 2012/0066781 A1 | 3/2012 | Weiner et al. |
| 2016/0007633 A1 | 1/2016 | Han et al. |
| 2016/0083700 A1 | 3/2016 | Tan et al. |
| 2016/0194618 A1 | 7/2016 | Solbak |

FOREIGN PATENT DOCUMENTS

| | | |
|---|---|---|
| AU | 724521 B2 | 9/2000 |
| CN | 100406561 C | 7/2008 |
| CN | 101418276 A | 4/2009 |
| CN | 101883500 | 11/2010 |
| CN | 102586294 A | 7/2012 |
| CN | 102943083 A | 2/2013 |
| EP | 1645195 | 4/2006 |
| EP | 1659173 A1 | 5/2006 |
| EP | 1806124 | 7/2007 |
| GB | 2331520 | 5/1999 |

(Continued)

OTHER PUBLICATIONS

Watanabe, et al, (2009). Cloning and characterization of a novel phytase from wastewater treatment yeast Hansenula fabianii J640 and expression in Pichia pastoris. Journal of Bioscience and Bioengineering. 108(3), 225-230.

(Continued)

*Primary Examiner* — Jennifer M. H. Tichy
(74) *Attorney, Agent, or Firm* — Richa Dhindsa

(57) ABSTRACT

A liquid enzyme formulation, an enzyme granule formulation, methods for manufacturing enzyme granules using a fluid bed dryer, wherein the enzyme granules are thermostable without the need for a thermostable coating is provided. The enzyme granules are phytase granules used in the manufacturing of an animal feed, wherein the phytase granule is thermostable without the need for a thermostable coating and the phytase retains about 63% to about 134% of its activity after pelleting at 80° C.

11 Claims, No Drawings

(56) References Cited

FOREIGN PATENT DOCUMENTS

| | | | | |
|---|---|---|---|---|
| JP | 2009-511068 | 3/2009 | | |
| JP | 2010-506564 | 3/2010 | | |
| JP | 2012-527247 | 11/2012 | | |
| RO | 118620 | 8/2003 | | |
| TW | 200306203 | 11/2003 | | |
| WO | WO 93/16175 A1 | 8/1993 | | |
| WO | WO 1999/008539 | 2/1999 | | |
| WO | WO 00/20569 A1 | 4/2000 | | |
| WO | WO 2000/071728 | 11/2000 | | |
| WO | WO 2001/029170 | 4/2001 | | |
| WO | WO 2001/090333 | 11/2001 | | |
| WO | WO 2002/095003 | 11/2002 | | |
| WO | WO 2003/037102 | 5/2003 | | |
| WO | WO 03/057247 A1 | 7/2003 | | |
| WO | WO 2005/007813 | 1/2005 | | |
| WO | WO 2005/056835 | 6/2005 | | |
| WO | WO 2005/074705 | 8/2005 | | |
| WO | WO 2006/028684 | 3/2006 | | |
| WO | WO 2007/142954 | 12/2007 | | |
| WO | WO 2008/036916 | 3/2008 | | |
| WO | WO 2009/018449 | 2/2009 | | |
| WO | WO 2009/073399 | 6/2009 | | |
| WO | WO 2010/096673 | 8/2010 | | |
| WO | WO 2010/135588 | 11/2010 | | |
| WO | WO 2011/0117396 | 9/2011 | | |
| WO | WO 2011/141613 | 11/2011 | | |
| WO | WO 2012/025462 | * | 3/2012 | ............... A23L 2/52 |
| WO | WO 2014/159185 | 10/2014 | | |
| WO | WO 2014/164442 | 10/2014 | | |

OTHER PUBLICATIONS

Wu, et al, (2004). Intracellular Expression of Bacillus Subtilis Phytase PhyC in Pichia Pastoris. Journal of Jishou University. 25(1), 36-41.
Xiong et al, (2006) High level expression of a synthetic gene encoding Peniophora lycii phytase in methylotrophic yeast Pichia pastoris. Applied Microbiology and Biotechnology, 72(5), 1039-1047.
Extended European Search Report, dated Oct. 12, 2016, in European Patent Application No. EP14780237.5, filed Sep. 20, 2015.
Altschul, et al. (1997), "Gapped BLAST and PSI-BLAST: a new generation of protein database search programs", Nuc. Acids Res., 25(17):3389-3402.
Altschul et al. (1990), Basic Local Alignment Search Tool. J. Mol. Biol. 215(3):403-410.
Altschul et al. (1994), Issue in searching molecular sequence databases. Nature Genetics 6:119-129.
Blobel G, Walter P, Chang CN, Goldman B, Erickson AH, and Lingappa VR (1979) Translocation of proteins across membranes: The signal hypothesis and beyond. Symp. Soc. Exp. Biol. 33:9-36.
Bairoch, A. (2000), "The Enzyme database in 2000". Nucleic Acids Res. 28:304-305.
Demain, (2009) "Production of Recombinant Proteins by Microbes and higher Organisms," Biotechnology Advances, vol. 27, pp. 297-306.
Garcia et al. (1987), Wild type and mutant signal peptides of *Escherichia coli* outer membrane lipoprotein interact with equal efficiency with mammalian signal recognition particle J. Biol. Chem. 262, 9463-9468.
Gizzi (2008), "Determination of Phytase Activity in Feed: Interlaboratory Study", J. of AOAC International. vol. 91, No. 2, pp. 259-267.
Mata et al., (1997), "A hexameric phosphorothioate oligonucleotide telomerase inhibitor arrests growth of Burkitt's lymphoma cells in vitro and in vivo", Toxicol. Appl. Pharmacol. 144:189-197.
Ng DT, Brown JD, Walter P. (1996) Signal sequences specify the targeting route to the endoplasmic reticulum membrane. J Cell Biol. 134:269-278.
Pariza (2010), "Determining the safety of enzymes used in animal feed," Regulatory Toxicology and Pharmacology 56(3):332-342.
Pearson et al., (1988), "Improved tools for biological sequence comparison", Proc. Natl. Acad. Sci. USA 85(8):2444-2448.
Powers T. and Walter P. (1996) The nascent polypeptide-associated complex modulates interactions between the signal recognition particle and the ribosome. Curr. Biol., 6, 331-338.
Rice (1992), "Random PCR mutagenesis screening of secreted proteins by direct expression in mammalian cells", Proc. Natl. Acad. Sci. USA 89:5467-5471.
Samstag (1996), "Synthesis and properties of new antisense oligodeoxynucleotides containing benzylphosphonate linkages", Antisense Nucleic Acid Drug Dev 6(3):153-156.
Sapkota (2007), "What Do We Feed to Food-Production Animals? A Review of Animal Feed Ingredients and Their Potential Impacts on Human Health", Environ Health Perspect. May, 115(5): 663-670.
Selle et al. (2007), "Microbial phytase in poultry nutrition", Animal Feed Science and Technology, 135(1-2):1-41.
Sijmons et al., (1990), "Production of correctly processed human serum albumin in transgenic plants", Biotech. 8(3):217-221.
Strauss-Soukup et al. (1997), "Effects of neutralization pattern and stereochemistry on DNA bending by methylphosphonate substitutions", Biochemistry 36(29):8692-8698.
Thompson et al. (1994), "CLUSTAL W: improving the sensitivity of progressive multiple sequence alignment through sequence weighting, position-specific gap penalties and weight matrix choice", Nucleic Acids Res. 22(22):4673-4680.
Von Heijne G. (1986), "A new method for predicting signal sequence cleavage sites", Nucleic Acids Res. Jun. 11, 1986; 14(11): 4683-4690.
International Preliminary Report on Patentability for International Patent Application No. PCT/US2014/022432 dated Sep. 24, 2015.
International Preliminary Report on Patentability for International Patent Application No. PCT/US2014/022433 dated Sep. 24, 2015.
International Preliminary Report on Patentability for International Patent Application No. PCT/US2014/022395 dated Feb. 4, 2016.
International Search Report and Written Opinion for International patent Application No. PCT/US2014/022432 dated Jul. 8, 2014.
International Search Report and Written Opinion for International Patent Application No. PCT/US2014/022395 dated Aug. 18, 2014.
International Search Report and Written Opinion for International patent Application No. PCT/US2014/022433 dated Jun. 16, 2014.
Supplementary Partial European Search Report dated Aug. 10, 2016, in European Application No. EP14774900, filed Oct. 6, 2015.
Gu Weina, Gene Cloning, Expression and Characterization of Four Phytases from *Enterobacteriaceae*, Chinese Doctoral Dissertations Full-text Database Basic Sciences, No. 5, A006-27. Published Nov. 15, 2017.
First Office Action, dated Jun. 1, 2017, in Chinese Patent Application No. 201480014287.1, filed Sep. 11, 2015.
European Extended Search Report, dated May 26, 2017, in European Patent Application No. EP 14829460.6, filed Feb. 17, 2016.
Altschul et al., Basic Local Alignment, 1990; J Mol Biol. (1990) 215(3):403-410.
Ausubel et al., [Eds.]Current Protocols in Molecular Biology; John Wiley & Sons, Inc. (1998), TOC; 15 pages.
Bairoch, A.; The Enzyme database in 2000; Nucleic Acids Res. (2000) 28:304-305.
Bickerstaff G.F. [Ed.] Immobilization of Enzymes and Cells: Some Practical Consideration; in Methods in Biotechnology, Humana Press, Totwa, NJ; (1997) Chapter 1, 16 pages.
Blobel et al., Translocation of proteins across membranes: The signal hypothesis and beyond. Symp Soc Exp Biol. (1979) 33:9-36; 18 pages.
Bonatti et al., Absence of a Cleavable Signal Sequence in Sindbis Virus Glycoprotein PE2; J Biol Chem. (1979) 254(24):12361-12364.
Chica et al., Semi-rational approaches to engineering enzyme activity: combining the benefits of directed evolution and rational design. Curr Opin Biotech. (2005) 16:(4):378-384.
Crameri et al., "Combinatorial multiple cassette mutagenesis creates all the permutations of mutant and wild-type seapences", Biotechniques, (1995); 18(2):194-196.
Demain et al., Production of recombinant proteins by microbes and higher organisms. Biotech Advances (2009) 27:297-306.

(56) References Cited

OTHER PUBLICATIONS

Higgins et al., "Using CLUSTAL for multiple sequence alignments", Methods Enzymol., (1996) 266:383-402.
Sijmons et al., Production of correctly processed human serum albumin in transgenic plants, Nature Biotech. (1990), 8(3):217-221.
Tijssen P., Hybridization with Nucleic Acid Probes: Part I: Theory and nucleic acid preparation; Elsevier Science Publishers BV (1993) Chapter 2; Overview; 62 pages.
Chinese Office Action, dated Dec. 30, 2016, in corresponding Chinese Patent Application No. 201480013617.5, filed Sep. 10, 2016.
Office Action, dated Feb. 10, 2017, in corresponding U.S. Appl. No. 14/904,840, filed Jan. 13, 2016.
Chica et al., Curr Opin Biotechnol, Aug. 2005, 16(4):378-84.
Sen et al., Appl Biochem Biotechnol, Dec. 2007, 143(3):212-23.
Yan et al. 2009. Comparative effects of phytase derived from *Escherichia coli* and *Aspergillus niger* in sixty eight-week-old laying hens fed corn-soy diet. *Asian-Aust. J. Anim. Sci.*, 22(10):1391-1399.
Office Action dated Aug. 28, 2017 in Taiwanese Patent Application No. 103108256 filed Mar. 10, 2014.
European Examination Report, dated May 29, 2017 in European Patent Application No. EP14780237.5 filed Sep. 17, 2015.
Office Action dated Feb. 6, 2018 in Japanese Patent Application No. 2016-529752 filed Jan. 22, 2016.
Office Action dated Mar. 8, 2018 in U.S. Appl. No. 14/904,840, filed Jan. 13, 2016.
Office Action, dated Aug. 25, 2017 in Taiwanese Patent Application No. 103108206 filed Mar. 10, 2014.
Office Action dated Dec. 22, 2017, in Chinese Patent Application No. 201480013617 filed Sep. 10, 2015.
Office Action dated Jul. 5, 2017 in European Application No. 14774900.6 filed Oct. 6, 2015.
Chinese Office Action dated Jul. 16, 2018 for Application No. 201480013617.5, filed Sep. 10, 2015.
EPO Notice on Oral Proceedings dated Jul. 16, 2018 for Application No. 14774900.6, filed Oct. 6, 2015.
Japanese Office Action dated Feb. 6, 2018 for Patent Application No. 2016-500966, filed Sep. 10, 2015.
European Partial Search Report dated May 17, 2018 for Patent Application No. 17211080.1, filed Dec. 29, 2017.
European Extended Search Report dated May 17, 2018 for Patent Application No. 17211080.1, filed Dec. 29, 2017.

* cited by examiner

PHYTASE FORMULATION

CROSS-REFERENCED TO RELATED APPLICATIONS

This application is a U.S. National Phase Application of PCT International Application Number PCT/US2014/022433, filed on Mar. 10, 2014, designating the United States of America and published in the English language, which is an International Application of and claims the benefit of priority to U.S. Provisional Application Ser. No. 61/784,947, filed on Mar. 14, 2013; and also claims the benefit of priority to Great Britain Patent Application Serial No. GB 1308843.0, filed on May 16, 2013. The disclosures of the above-referenced applications are herein expressly-incorporated by reference in their entireties.

TECHNICAL FIELD

This invention relates to a liquid enzyme formulation, a granulated enzyme formulation, and methods for manufacturing enzyme granules using a fluid bed dryer wherein the enzyme granules are thermostable without the need for a thermostable coating.

Processes for manufacturing animal feed are well established. Industrial scale production of animal feed generally involves: obtaining a feedstock, grinding the feedstock, mixing the feedstock with dry and/or liquid ingredients, pelleting, and drying.

Feedstocks, which are the raw ingredients of the animal feed, come from a variety of sources including: plants; animals; edible by-products; and additives, such as vitamins, minerals, enzymes, and other nutrients (SAPKOTA; Environ Health Perspect. 2007 May; 115(5): 663-670).

Animal feed additives, such as enzymes, are designed to increase the nutritional value of the feed by releasing nutrients and allowing increased absorption of essential vitamins and minerals in the animal, which in turn, enhances animal product yield, while reducing harmful materials in animal waste.

Enzymes used as additives in the manufacturing of animal feed include, but are not limited to: a phytase, cellulase, lactase, lipase, protease, catalase, xylanase, beta-glucanase, mannanase, amylase, amidase, epoxide hydrolase, esterase, phospholipase, transaminase, amine oxidase, cellobiohydrolase, ammonia lyase, or any combination thereof.

Enzymes are normally introduced into animal feed manufacturing process as a dry enzyme granule or as a liquid enzyme formulation. The selection of a dry enzyme formulation or liquid enzyme formulation depends upon the operation conditions used at an animal feed mill. For example, temperatures range from 37 degrees C. to 95 degrees C. or more during mixing and pelleting process of animal feed production.

Liquid enzyme formulations may be added to the feed or food after pelleting in order to avoid heat inactivation of the enzyme(s) which would occur during the pelleting process. However the amounts of enzyme in the final feed or food preparations are usually very small which makes it difficult to achieve a homogenous distribution of the enzyme in the feed or food, and liquids are notoriously more difficult to mix evenly than dry ingredients. In addition one needs specialised (expensive) equipment to add liquids to the feed after pelleting which is not currently available at most feed mills (due to the extra cost). Even when applying liquid formulations comprising enzymes, the storage stability of such formulations often is a problem, see WO 2005/074705.

A dry or granulated enzyme formulation may be added to the mixer prior to the pelleting process. However, the high temperatures used during the mixing and pelleting process usually require a specially coated granulated enzyme formulation in order for the enzyme to remain active in the final feed pellets. Additionally, enzymes are usually manufactured in a liquid formulation, thus the process of drying an enzyme into a granule, coating the granule, transporting granules to the feed mill, and adding the granules to the feed mixer present added costs and time.

There are a variety of granulation technologies including, but not limited to extrusion, high-shear granulation, and fluidized-bed granulation.

Extrusion and spheronization is a process for producing granule by mixing an enzyme, a carrier, and extruding the mixture to form granules.

High-shear granulation generally includes mixing dry ingredients and liquid ingredients with a mixing blade, chopper and/or impeller. The mixing can be at a high intensity or low intensity.

Fluid bed granulation involves a single container where the ingredients are suspended in a heated air, agglomeration of ingredients occurs, granules dry, and fall to the bed. An advantage of fluid bed granulation is that it reduces unit operations and manufacturing time. However, the hot air can denature, reduce the activity of an enzyme, or both. Therefore a need exists to provide a thermo-stable enzyme, and enzyme formulation, or a combination thereof that can be used in a fluid bed granulation process.

In one embodiment, the enzyme granules produced are used as additives for animal feed.

A variety of animals can benefit from animal feed containing an enzyme including: non-ruminant animals, e.g. poultry, broilers, birds, chickens, layers, turkeys, ducks, geese, and fowl; ruminant animals e.g. cows, cattle, horses, and sheep; pigs, swine, piglets, growing pigs, and sows; companion animals including but not limited to: cats, dogs, rodents, and rabbits; fish including but not limited to salmon, trout, tilapia, catfish and carp; and crustaceans including but not limited to shrimp and prawn.

DETAILED DESCRIPTION

An "enzyme" as used herein refers to any enzyme that can be used as an additive for animal feed. For example, enzymes useful in the present invention include, but are not limited to: a phytase, lactase, lipase, protease, catalase, xylanase, cellulase, glucanase, mannanase, amylase, amidase, epoxide hydrolase, esterase, phospholipase, transaminase, amine oxidase, cellobiohydrolase, ammonia lyase, or any combination thereof.

A "phytase" is an enzyme that catalyzes the removal of one or more phosphate groups from a phytate substrate. In another embodiment, a phytase is a phosphoric monoester hydrolase enzyme that catalyzes hydrolysis of phytic acid (myo-inositol-hexakisphosphate) to phosphate and myo-inositol having fewer than six phosphate groups. According to the recommendations of the Nomenclature Committee of the International Union of Biochemistry and Molecular Biology (IUBMB) and Bairoch A., "The ENZYME database in 2000," Nucleic Acids Res 28:304-305(2000), a phytase may be described in a variety of names and identifying numbers. In another embodiment, a phytase is characterized as having Enzyme Commission (EC) number EC 3.1.3.8, and are also referred to as: 1-phytase; myo-inositol-hexakisphosphate 3-phosphohydrolase; phytate 1-phosphatase; phytate 3-phosphatase; or phytate 6-phosphatase. In another embodiment, a phytase is characterized as EC 3.1.3.26, also referred to as: 4-phytase; 6-phytase (name based on 1L-numbering system and not 1D-numbering); or phytate 6-phosphatase. In another embodiment, a phytase is characterized as EC 3.1.3.72, also referred to as 5-phytase. In another embodiment, a phytase is a histidine acid phosphatase (HAP); a β-propeller phytase; purple acid phosphatase (PAP); and protein tyrosine phosphatase (PTPs). In some embodiments, a phytase is described using nomenclature know in the art.

An "inositol phosphatase" is an enzyme that catalyzes the removal of one or more phosphate groups from an inositol phosphate molecule.

A "phytate" or phytic acid is myo-inositol hexaphosphate. It is the fully-phosphorylated form of inositol phosphate.

An "inositol phosphate" is myo-inositol that is phosphorylated at one or more of its hydroxyl positions.

A "cellulase" is an enzyme that catalyzes the hydrolysis of a polymeric carbohydrate compound such as cellulose, glucomannan, mannan, glucan, and xyloglucan, for example.

A "xylanase" is an enzyme that catalyzes the degradation of the linear polysaccharide beta-1,4-xylan into xylose.

A "glucanase" is an enzyme that catalyzes the degradation of glucans comprising glucose sub-units. Examples of glucanases include alpha-1,4-glucanases, alpha-1,6 glucanases, pullulanases, beta-1,3,-glucanases, beta-1,4-glucanases, and beta-1,6-glucanases.

A "mannanase" is an enzyme that catalyzes the degradation of mannose polysaccharide polymers.

An "amylase" is an enzyme that catalyzes the hydrolysis of 1,4-alpha-D-glucosidic linkages to degrade polysaccharides, oligosaccharides, and/or starch into glucose subunits.

The term "comprising" as used herein is synonymous with "including," "containing," or "characterized by," and is inclusive or open-ended and does not exclude additional, unrecited elements or method steps.

An enzyme is "thermostable" if it retains a substantial amount of its activity after a high temperature treatment of at least about 65° C. to about 95° C.; or at a temperature greater than 95° C.

In some embodiments, the thermostable enzyme retains at least: 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of its activity after a pelletization process. In an embodiment, the pelletization process is conduct at a temperature of at least: 75° C., 80° C., 85° C., 88° C., 90° C., or 93° C.

A "combination of enzymes" is any combination of enzymes that may be used as additives for an animal feed. Examples of such combinations of enzymes are set forth in Table 1.

TABLE 1

| Combination of Enzymes | Phytase | Xylanase | Glucanase | Amylase | Protease |
|---|---|---|---|---|---|
| 1 | X | X | | | |
| 2 | X | | X | | |
| 3 | X | | | X | |

TABLE 1-continued

| Combination of Enzymes | Phytase | Xylanase | Glucanase | Amylase | Protease |
|---|---|---|---|---|---|
| 4 | X | | | | X |
| 5 | X | X | X | | |
| 6 | X | X | | X | |
| 7 | X | X | | | X |
| 8 | X | | X | X | |
| 9 | X | | X | | X |
| 10 | X | | | X | X |
| 11 | X | X | X | X | |
| 12 | | X | X | X | X |
| 13 | X | X | X | | |
| 14 | | X | | X | |
| 15 | | | | | |
| 16 | X | | | | X |
| 17 | | X | X | | |
| 18 | | X | | | X |
| 19 | | | | X | X |
| 20 | | | X | X | X |
| 21 | X | X | X | X | X |

As used herein "liquid enzyme formulation" is a composition comprising an enzyme, a buffer, a stabilizer, and an anti-microbial.

In one embodiment, a liquid enzyme formulation comprises an enzyme, wherein the enzyme is a phytase, a cellulase, a lactase, a lipase, a protease, a catalase, a xylanase, a beta-glucanase, a mannanase, an amylase, an amidase, an epoxide hydrolase, an esterase, a phospholipase, a transaminase, an amine oxidase, a cellobiohydrolase, an ammonia lyase, or any combination thereof.

In one embodiment, a liquid enzyme formulation comprises a buffer includes, but is not limited to sodium citrate, potassium citrate, citric acid, sodium acetate, acetic acid, sodium phosphate, potassium phosphate and any combination thereof.

In one embodiment, a liquid enzyme formulation comprises a stabilizer, wherein the stabilizer is a sodium chloride, a sorbitol, a glycerol, a sucrose, a mannitol, a trehalose, or any combination thereof. In another embodiment, a liquid enzyme formulation may include two stabilizers.

In one embodiment, a liquid enzyme formulation comprises an anti-microbials, wherein the anti-microbial is a potassium sorbate; a sodium sorbate, a sorbic acid; a sodium benzoate; a benzoic acid a calcium propionate, a sodium propionate, an ammonium propionate; a propionic acid or any combination thereof.

In one embodiment, the liquid enzyme formulation is set forth in Table 2:

| Category | Options | Ingredient | Concentration (% w/v) |
|---|---|---|---|
| Enzyme | | phytase | 10,000 units/ml (5,000-20,000 unit/ml) |
| Buffer | | sodium citrate, pH 5.0 (4.5-5.5) | 1.25% (0.5-2.5%) |
| Stabilizer | 1 | sodium chloride | 15% (1-20%) |
| | 2 | sorbitol | 20% (2-40%) |
| | 3 | glycerol | 20% (2-40%) |
| | 4 | sucrose | 20% (2-40%) |
| Anti-microbial | 1 | potassium sorbate | 0.20% (0.05-0.40%) |
| | 2 | sodium benzoate | 0.20% (0.05-0.40%) |
| | 3 | methyl paraben | 0.20% (0.05-0.40%) |
| | 4 | calcium/sodium/ammonium propionate | 0.20% (0.05-0.40%) |

In one embodiment, the liquid enzyme formulation is a liquid product, wherein the liquid product is applied to the post pelleting. In another embodiment, the liquid product is an enzyme, sodium chloride, sorbitol, sodium citrate, potassium sorbate, and sodium benzoate. In another embodiment, the liquid product is a composition having a Phytase having 11,000-12,000 unit/g, a sodium chloride 15%, a sorbitol 4%, a sodium citrate 50 mM, a potassium sorbate 0.2%, a sodium benzoate 0.1%, and a sodium propionate 0.1% (all % are w/v %). In another embodiment, the liquid product is a composition having a Phytase having 11,000-12,000 unit/g, a sodium chloride 15%, a sucrose 6%, a sodium citrate 50 mM, a potassium sorbate 0.2%, a sodium benzoate 0.1%, sodium propionate 0.1% (all % are w/v %).

In one embodiment, the liquid enzyme formulation is a liquid concentrate, wherein the liquid concentrate is added to the feed mash prior to the pelleting process. In one embodiment, the liquid concentrate is an enzyme, and sucrose, and sodium chloride, and sodium citrate and potassium sorbate, sodium benzoate, and sodium propionate. In another embodiment the liquid concentrate is a composition comprising: a Phytase having 44,000-48,000 unit/g, 20% sucrose, 1% NaCl, 50 mM sodium citrate, pH 5.1, 0.1% sodium benzoate, 0.4% potassium sorbate, 0.4% sodium propionate. In another embodiment the liquid concentrate is a composition comprising: a Phytase having 44,000-48,000 unit/g, 2%-40% sorbitol, 1% NaCl, 50 mM sodium citrate, a pH 4.5, 4.6, 4.7, 4.8, 4.9, 5.0, 5.1, 5.2, 5.3, 5.4, or 5.5, 0.1% sodium benzoate, 0.4% potassium sorbate, 0.4% sodium propionate. In another embodiment, the liquid concentrate is not the final product, but is an intermediate composition or formulation that is later used for the production of a liquid product a granulated dry product.

As used herein "a granulated enzyme formulation" is a composition comprising: a carrier; a primary solution comprising an enzyme, a buffer, a stabilizer, a binding agent, a plasticizer, an anti-microbial, or any combination thereof. In another embodiment, a granulated enzyme formulation is a composition comprising: a carrier; a primary solution comprising an enzyme, a buffer, a stabilizer, a binding agent, a plasticizer, an anti-microbial, and a secondary solution comprising an enhancer, a plasticizer, or any combination thereof. In one embodiment, a granulated enzyme formulation is thermostable without the need for the enzyme granule to have a protective coating. In another embodiment, the granulated product is an enzyme, sucrose, sodium chloride, sodium citrate, potassium sorbate, sodium benzoate, sodium propionate, guar gum, wheat flour.

In one embodiment, the primary solution is a liquid enzyme formulation. In another embodiment, the liquid enzyme formulation is a liquid product or a liquid concentrate.

In one embodiment, a granulated enzyme formulation comprises a carrier, wherein the carrier is a flour. In another embodiment, the carrier is a starch. In an embodiment, the flour is a wheat flour. In another embodiment, the wheat flour is bleached wheat flour. In another embodiment, the carrier is a wheat flour and a maltodextrin. In another embodiment, the carrier is a wheat flour and a pre-gelatinized starch. In another embodiment, the maltodextrin or pre-gelatinized starch is used as a dry mixture with flour. In another embodiment, the flour is a wheat flour, or bleached flour. In an embodiment, the maltodextrin or pre-gelatinized starch is used as a dry mixture. In an embodiment, the wheat flour and kaolin is a dry mixture.

In one embodiment, a granulated enzyme formulation comprises an enzyme, wherein the enzyme is a phytase, a cellulase, a lactase, a lipase, a protease, a catalase, a xylanase, a beta-glucanase, a mannanase, an amylase, an amidase, an epoxide hydrolase, an esterase, a phospholipase, a transaminase, an amine oxidase, a cellobiohydrolase, an ammonia lyase, or any combination thereof.

In one embodiment, a granulated enzyme formulation comprises a buffer, wherein the buffer is a sodium citrate, potassium citrate, citric acid, sodium acetate, acetic acid, sodium phosphate, potassium phosphate and any combination thereof.

In one embodiment, a granulated enzyme formulation comprises a stabilizer, wherein the stabilizer is a sucrose, a sodium chloride, a sorbitol, a glycerol, a sucrose, a mannitol, a trehalose, kaolin, aluminum silicate, magnesium silicate or any combination thereof.

In one embodiment, a granulated enzyme formulation comprises a binding agent, wherein the binding agent is a guar gum, a xanthan, a sodium algenate, a locust bean gum, a carrageenan gum, a pre-gelatinized modified starch, a maltodextrin, gelatin, methyl cellulase, hydroxypropyl cellulase, hydroxypropyl methyl cellulase, carboxymethyl cellulase, or any combination thereof. In another embodiment, the natural gums may be used individually or as a combination of at least two gums. In another embodiment, starch or maltodextrin are used in combination with guar gum. In another embodiment, starch or maltodextrin also act as a stabilizer.

In one embodiment, a granulated enzyme formulation comprises a plasticizer, wherein the plasticizer is selected from a group consisting of: a glycerol, polyethylene glycol, triethyl citrate, triacetin, acetyl triethylcitrate.

In one embodiment, a granulated enzyme formulation comprises an anti-micorbial, wherein the anti-micorbial is a potassium sorbate, sodium sorbate, sorbic acid, propionic acid, sodium benzoate, benzoic acidsodium propionate, calcium propionate, ammonium propionate, methyl paraben, or any combination thereof. In another embodiment, at least two anti-micoribals are used in the granulated enzyme formulation.

In one embodiment, a granulated enzyme formulation comprises a secondary granulation solution, wherein the secondary granulation solution is a composition comprising a granule enhancer and a plasticizer. In another embodiment, the secondary granulation solution enhances the granule size, creates grater variability, or both. In another embodiment, the granule size is any numerical mesh size between the range from about 12 mesh to about 100 mesh size. In another embodiment, the granule size is any numerical mesh size between the range between from about 20 mesh to about 80 mesh. In another embodiment, the granule size is any numerical mesh size between the range from about 30 mesh to about 60 mesh.

In one embodiment, a granulated enzyme formulation comprises a granule enhancer, wherein the granule enhancer is pre-gelatinized modified starch, maltodextrin, sodium algenate, carregeenan with CaCl2, carregeenan without CaCl2, guar gum with sodium borate, guar gum without sodium borate, gelatin; methyl celluloase; hydroxypropyl cellulose; hydroxypropyl methyl celluloase; carboxymethyl celluloase; sodium chloride; sodium sulphate; kaolin; aluminum silicate, magnesium silicate, and any combination thereof. In another embodiment, the enhancer is an optional addition to the granulated enzyme formulation. In another embodiment, the natural gum and ion combination will cross link the gum into protective gel; however, if the gum is already used as binding agent, then the addition of ion alone will suffice without the addition of extra gum.

In one embodiment, a granulated enzyme formulation comprises a plasticizer, wherein the plasticizer is a glycerol.

In another embodiment, glycerol may be used when pre-gelatinized modified starch is used.

In one embodiment, a granulated enzyme formulation further comprising a flow aid or lubricant, wherein the flowing aid is selected from a group consisting of: a silicon dioxide, a magnesium stearate, a kaolin, a talc, diatomaceous earth, or any combination thereof. In another embodiment, the addition of a granulated enzyme formulation is a flowing aid or lubricant is optional. In another embodiment, the flowing aid or lubricant is a dry blend post drying. In another embodiment, the flowing aid or lubricant is added as a suspension in the secondary granulation solution. In another embodiment, the granulated dry product is a composition comprising: a Phytase having 11,000-12,000 unit/g, a sucrose 4.5%, a sodium citrate 0.3%, a potassium sorbate 0.1%, sodium benzoate 0.1%, sodium propionate 0.1%, guar gum 0-0.25%, and a wheat flour 95% (all % are w/w %).

In one embodiment, a granulated enzyme formulation is set forth in Table 3:

the present application, each numerical parameter should be construed in light of the number of significant digits and ordinary rounding approaches. In addition, the numerical ranges disclosed in this application are inclusive and disclose all of the numerical digits within a range. For example a range of pH from 4.5 to 5.5 includes a pH of 4.5, 4.6, 4.7, 4.8, 4.9, 5.0, 5.1, 5.2, 5.3, 5.4, and 5.5.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

| Material | Category | Options | Ingredient | Concentration in liquid feed (% w/v) | Amount per kg of dried product (g) |
|---|---|---|---|---|---|
| Carrier | Carrier | 1 | wheat flour | | 850-950 g |
| | | 2 | wheat flour | | 700-800 g |
| | | | maltodextrin or pre-gelatinized starch | | 100-200 g |
| Enzyme solution/ Primary granulation solution | Enzyme | | phytase | 40,000 unit/ml (10,00-50,000 unit/ml) | 10,000 unit/g (5,000-20,000 unit/g) |
| | Buffer | | sodium citrate, pH 5.0 (4.5-5.5) | 1% (0.5-2.0%) | 3 g (1.5-6.0 g) |
| | Stabilizer | 1 | sucrose | 20% (10-30%) | 50 g (25-100 g) |
| | | 2 | sodium chloride, or sodium sulphate | 1% (0.5-10%) | 2 g (1-20 g) |
| | Binding agent | 1 | guar gum | 0.5% (0.2-1%) | 1.25 g (0.5-2.5 g) |
| | | 2 | xanthan, sodium algenate, locust bean gum, or carrageenan | 0.5% (0.2-1%) | 1.25 g (0.5-2.5 g) |
| | | 3 | pre-gelatinized modified starch (corn) | 5% (2-10%) | 12.5 g (5-25 g) |
| | | 4 | maltodextrin | 10% (5-20%) | 25 g (12.5-50 g) |
| | Plasticizer | | glycerol | 0.5% (0.2-1%) | 1.25 g (0.5-2.5 g) |
| | Anti-microbial | 1 | potassium sorbate | 0.4% | 1.0 g |
| | | 2 | sodium benzoate | 0.4% | 1.0 g |
| | | 3 | sodium/calcium/ammonium propionate | 0.4% | 1.0 g |
| | | 4 | methyl paraben | 0.10% | 0.25 g |
| Secondary granulation solution | Granule enhancer | 1 | pre-gelatinized modified starch (corn) | 12% (10-15%) | 25 g (5-50 g) |
| | | 2 | maltodextrin | 25% (10-50%) | 50 g (25 g-100 g) |
| | | 3 | sodium algenate or carrageenan with CaCl2 | 5% (2-10%) | 10 g (5 g-25 g) |
| | | 4 | guar gum with sodium borate | 0.5% (0.2-1.0%) | 1.25 g (0.5-2.5 g) |
| | | 5 | sodium chloride, or sodium sulphate | 20% (10-30%) | 40 g (20 g-80 g) |
| | | 6 | Kaolin | 10% (1-20%) | 20 g (10-40 g) |
| | Plasticizer | | glycerol | 1.2% (0.2-1%) | 2.5 g (1-5 g) |
| Flowing aid/lubricant | Flowing aid/lubricant | 1 | silicon dioxide | | 10 g (1-20 g) |
| | | 2 | magnesium stearate | | 10 g (2.5-15 g) |
| | | 3 | kaolin | | 20 g (5-50 g) |
| | | 4 | talc | | 30 g (10-100 g) |

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

EXAMPLES

Example 1

Comparative Example of Non-Granulated Phytase

Formulation 1—A liquid concentrate phytase formulation containing 10% sodium chloride and 10% sorbitol was dried by lyophilization. The dried enzyme powder was then diluted by mixing with calcium carbonate and rice hulls to form a rice hull enzyme product.

Formulation 2—A liquid concentrate phytase formulation containing 10% sodium chloride and 10% sorbitol was soaked on the rice hulls. The resulting wet blend was dried by lyophilization. The dried material was diluted by mixing with calcium carbonate to form a rice hull enzyme product.

Pelleting Trials—The rice hull enzyme product was blended with poultry feed mash at 25-100 ppm concentration, and pelleted in a California Pellet Mill at various controlled temperatures in the range of 75° C. to 93° C. The mash mixture was first conditioned by direct steam at said temperature for 15 seconds, and then pelleted through the pelleting press. The pellets were subsequently dried.

Enzyme Stability Determination—The starting mash and finished pellets (which were milled down to mash) were extracted in a Tris buffer. Phytase activities in the extracts were determined by a modified AOAC method. The modified AOAC method is the AOAC buffer comprising distilled water plus 0.01% Tween 20 (GIZZI, J. of AOAC International, Vol. 91, No. 2, 2008) and was modified to a composition comprising: 50 mM Tris pH 8.0, 0.01% Tween20, 10 mM $CaCl_2$.

The percent recovery of the enzyme activity of pelleted product at each temperature was compared to that of the starting mash. The results are shown in Table 4.

TABLE 4

Residual Phytase activities (%) in poultry feed after pelleting at different conditioning temperatures

| Sample # | 75° C. | 80° C. | 85° C. | 88° C. | 90° C. | 93° C. |
| --- | --- | --- | --- | --- | --- | --- |
| Formulation 1 | 70% | 63% | 55% | 49% | 16% | 6% |
| Formulation 2 | 63% | 64% | 51% | 43% | 27% | 13% |

The results show that phytase activity extracted from the pelleted feed was lower at high conditioning temperatures for both formulation 1 and formulation 2.

Example 2

Formulation 3—250 g of rice hulls was loaded in a GEA Aeromatic-Fielder Strea-1 fluid bed granulator; 50 ml of a liquid concentrate phytase formulation containing 10% sorbitol and 10% sodium chloride was sprayed onto the rice hulls through a top spray two-fluid nozzle. The following fluid bed settings were used: 55° C. inlet air temperature, 5 ml/min spray rate, 1 bar atomizing pressure, 0.8 mm spray nozzle. The rice hull enzyme product was dried after the enzyme spray.

Formulation 4—200 g of rice hulls was loaded in a GEA Aeromatic-Fielder Strea-1 fluid bed granulator; 100 ml of a liquid concentrate phytase formulation containing 20% sucrose was sprayed onto the rice hulls through a top spray two-fluid nozzle. The fluid bed settings were the same as Formulation 3 and were used to form a rice hull enzyme product.

Formulation 5—200 g of wheat flour was loaded in a GEA Aeromatic-Fielder Strea-1 fluid bed granulator; 100 ml of a liquid concentrate phytase formulation containing 20% sucrose and 7% pre-gelatinized starch was sprayed onto the wheat flour through a top spray two-fluid nozzle. The following fluid bed settings were used: 50° C. inlet air temperature, 10-15 ml/min spray rate, 1.5-2 bar atomizing pressure, 0.8 mm spray nozzle. The wheat flour and enzyme product was dried after the enzyme spray to form phytase granules.

Pelleting Trials and Enzyme Stability Determination were the same as in Example 1. The results are shown in Table 5.

TABLE 5

Residual Phytase activities (%) in poultry feed after pelleting at different conditioning temperatures

| Sample # | 75° C. | 80° C. | 85° C. | 88° C. | 90° C. | 93° C. |
| --- | --- | --- | --- | --- | --- | --- |
| Formulation 3 | 67% | 70% | 80% | 56% | 29% | 9% |
| Formulation 4 | 72% | 75% | 58% | 56% | 36% | 17% |
| Formulation 5 | 95% | 89% | 93% | 79% | 77% | 38% |

Rice hulls were used as carrier in Formulations 3 & 4. The rice hulls were not finely milled and not very absorbent; in addition, no binder was used in these formulations. As a result, no effective granulation was seen in the rice hull enzyme products. The thermal stability for both formulations was relatively low at high conditioning temperatures when compared to Formulation 5. Switching the stabilizer from sodium chloride and sorbitol to sucrose improved thermostability of the phytase. However, when the carrier was switched from rice hulls to finely milled wheat flour in combination with the use of a pre-gelatinized starch as binder as in formulation 5. The wheat flour enzyme product was granulated, and the thermal stability of the phytase extracted from an animal feed pellet improved across all temperatures, especially at 90° C.

Example 3

Formulation 6—3 kg of wheat flour was loaded in a Vector VFC-Lab 3 fluid bed granulator; 1.6 kg of liquid concentrate phytase formulation containing 20% sucrose and 0.5% guar gum was sprayed onto the wheat flour through a top spray two-fluid nozzle. The fluid bed settings were 1.2 mm nozzle diameter, 20 psi atomizing pressure, 50-55° C. inlet air temperature, 23-27° C. product temperature, 25-50 g/min pray rate during spray; 70-80° C. inlet air temperature during drying, dried to 45° C. end product temperature to form phytase granules.

Formulation 7—3 kg of wheat flour was loaded in a Vector VFC-Lab 3 fluid bed granulator; 1.6 kg of liquid concentrate phytase formulation containing 20% sucrose, 10% maltodextrin and 0.5% guar gum was sprayed onto the wheat flour through a top spray two-fluid nozzle. The fluid bed settings were 1.2 mm nozzle diameter, 20 psi atomizing pressure, 50° C. inlet air temperature, 23-29° C. product temperature, 25-50 g/min pray rate during spray; 70-80° C. inlet air temperature during drying, dried to 45° C. end product temperature to form phytase granules.

Pelleting Trials and Enzyme Stability Determination were the same as in Example 1. The results are shown in Table 6. All residual activities were normalized to 75° C. stability of the same sample.

TABLE 6

Residual Phytase activities (%) in poultry feed after pelleting at different conditioning temperatures

| Sample # | 75° C. | 88° C. | 90° C. | 93° C. |
|---|---|---|---|---|
| Formulation 3 | 100% | 31% | 9% | |
| Formulation 6 | 100% | 92% | 35% | 5% |
| Formulation 7 | 100% | 76% | 40% | 4% |

Formulation 3 was the same sample from Example 2, and it was used as a control in this experiment. The thermal stability for formulation 3 is lower here than the value in Example 2, probably due to harsher pelleting conditions in this trial. Both Formulations 6 and 7 resulted in phytase granules that improved thermal stability of the phytase when extracted from a pelleted animal feed.

Additional Pelleting Trials—to confirm the improvement in thermal stability, the phytase granules produced from the two samples (Formulation 6 and 7) were subjected to additional pelleting trial using a different California Pellet Mill. The duration for steam conditioning was 40 seconds, which is significantly longer than the previous pelleting trials. The results are shown in Table 7. All residual phytase activities were normalized to 75° C. stability of the same sample.

TABLE 7

Residual Phytase activities (%) in poultry feed after pelleting at different conditioning temperatures.

| Sample # | 75° C. | 85° C. | 90° C. | 92° C. |
|---|---|---|---|---|
| Formulation 6 | 100% | 82% | 66% | 12% |
| Formulation 7 | 100% | 94% | 50% | 8% |

The results confirmed that even under prolonged steam conditioning, both phytase granules from Formulations 6 and 7 provided high phytase activity for phytase extracted from animal feed pellets generated at high pelleting temperature.

Example 4

Formulation 8—3 kg of wheat flour was loaded in a Vector VFC-Lab 3 fluid bed granulator; 1.6 kg of liquid concentrate phytase formulation containing 20% sucrose, 10% kaolin and 0.5% guar gum was sprayed onto the wheat flour through a top spray two-fluid nozzle. The fluid bed settings were 1.2 mm nozzle diameter, 20 psi atomizing pressure, 50° C. inlet air temperature, 22-30° C. product temperature, 25-50 g/min pray rate during spray; 70-80° C. inlet air temperature during drying, dried to 45° C. end product temperature to form phytase granules.

Formulation 9—3 kg of wheat flour was loaded in a Vector VFC-Lab 3 fluid bed granulator; 1.6 kg of liquid concentrate phytase formulation containing 20% sucrose, 10% maltodextrin, 5% kaolin and 0.5% guar gum was sprayed onto the wheat flour through a top spray two-fluid nozzle. The fluid bed settings were the same as in Formulation 8 to form phytase granules.

Formulation 10—2 kg of wheat flour was loaded in a Vector VFC-Lab 3 fluid bed granulator; 1 kg of liquid concentrate phytase formulation containing 20% sucrose and 0.5% guar gum was sprayed onto the wheat flour through a top spray two-fluid nozzle; 1 kg of secondary granulation solution was then sprayed containing 10% modified starch, 10% kaolin and 1% glycerol. The fluid bed settings during enzyme spray were the same as in Formulation 8; during secondary granulation solution spray, the spray rate was 17-18 g/min, inlet air temperature was 60° C., and the product temperature was 30-31° C.; during drying, inlet air temperature was 70-80° C. to form phytase granules.

Pelleting Trials and Enzyme Stability Determination were the same as in Example 1 and the results are shown in Table 8.

TABLE 8

Residual Phytase activities (%) in poultry feed after pelleting at different conditioning temperatures

| Sample # | 80° C. | 85° C. | 88° C. | 90° C. | 93° C. |
|---|---|---|---|---|---|
| Formulation 8 | 74% | 61% | 79% | 52% | 20% |
| Formulation 9 | 132% | 71% | 68% | 58% | 25% |
| Formulation 10 | 104% | 92% | 79% | 74% | 28% |

The results showed that the inclusion of kaolin in the secondary granulation solution spray led to increased phytase thermal stability; and the use of a secondary granulation solution further enhanced the phytase thermal stability of the phytase extracted from the animal feed pellet.

Example 5

Formulation 11—3 kg of wheat flour was loaded in a Vector VFC-Lab 3 fluid bed granulator; 1.3 kg of liquid concentrate phytase formulation containing 20% sucrose and 0.5% guar gum was sprayed onto the wheat flour through a top spray two-fluid nozzle. The fluid bed settings were 1.2 mm nozzle diameter, 20 psi atomizing pressure, 50° C. inlet air temperature, 22-29° C. product temperature, 25-50 g/min pray rate during spray; 70-80° C. inlet air temperature during drying, dried to 45° C. end product temperature to form phytase granules.

Formulation 12—4.6 kg of wheat flour was loaded in a 5-kg scale customized fluid bed granulator; 1.25 kg of liquid concentrate phytase formulation containing 20% sucrose and 0.5% guar gum was sprayed onto the wheat flour through a top spray two-fluid nozzle; 1 kg of secondary granulation solution containing 0.5% guar gum only was then sprayed. The fluid bed settings were 60-80° C. inlet air temperature, 28-36° C. product temperature and 40 g/min spray rate to form phytase granules.

Pelleting Trials and Enzyme Stability Determination were the same as in Example 1 and the results are shown in Table 9.

TABLE 9

Residual Phytase activities (%) in poultry feed after pelleting at different conditioning temperatures

| Sample # | 75° C. | 80° C. | 85° C. | 88° C. | 90° C. | 93° C. |
|---|---|---|---|---|---|---|
| Formulation 11 | 93% | 111% | 76% | 113% | 57% | 38% |
| Formulation 12 | 108% | 108% | 107% | 129% | 91% | 73% |

The results showed that both samples had improved phytase thermal stability; and the use of a secondary granulation solution further enhanced the thermal stability of the the phytase extracted from an animal feed pellet generated at high pelleting temperatures.

Example 6

Most thermally stable feed enzymes currently commercially available rely on thermal protective coating. Some of these coatings have been shown to inadvertently delay the enzyme release into the solution, which lead to reduced enzyme efficacy. Therefore, the time release profile of Phytase activity from the granulated product of the current invention was examined.

One hundred milligrams of granulated Phytase from Formulation 12 was mixed with 400 ul of 100 mM sodium acetate buffer at pH 5.5. The mixture was agitated for up to 60 minutes. At designated time point, an aliquot was removed and centrifuged. Phytase activity in the clear supernatant was assayed. The results are shown in Table 10.

TABLE 10

Time Release Profile of Phytase Activity

| | Time (minutes) | | | | |
|---|---|---|---|---|---|
| | 2.5 | 5 | 7.5 | 10 | 15 | 20 |
| Formulation 12 | 94% | 100% | 100% | 100% | 100% | 100% |

The results show that Phytase became soluble in very short amount of time. On the other hand, some commercially available thermal coated Phytase granules displayed significant delay in releasing the enzyme activity into the solution, by as much as 20 minutes (data not shown).

What is claimed is:

1. A liquid enzyme formulation comprising:
   (a) a phytase at a concentration of 5,000 to 50,000 unit/ml of the liquid enzyme formulation;
   (b) a buffer, at a concentration of 0.5%-2.5% w/v, wherein the buffer is selected from the group consisting of: a sodium citrate, potassium citrate, citric acid, sodium acetate, acetic acid, sodium phosphate, potassium phosphate and any combination thereof;
   (c) a stabilizer, at a concentration of 1%-40% w/v, wherein the stabilizer is selected from the group consisting of: a sucrose, a sorbitol, a mannitol, a glycerol, a trehalose, a sodium chloride, a sodium sulphate, or any combination thereof; and,
   (d) an anti-microbial, at a concentration of 0.05%-0.40% w/v, wherein the anti-microbial is selected from the group consisting of: a potassium sorbate, sodium sorbate, a sorbic acid, a sodium benzoate, a benzoic acid, a methyl paraben, a calcium propionate, a sodium propionate, an ammonium propionate, a propionic acid, or any combination thereof,
   wherein the phytase retains at least 63% of its activity at a temperature of 80° C.

2. The liquid enzyme formulation of claim 1, wherein
   (a) the buffer has a pH in a range from 4.5 to about 5.50,
   (b) the stabilizer is a combination of at least two stabilizers,
   (c) the stabilizer is at a concentration between 5% to 30%, or
   (d) the anti-microbial is a combination of at least two anti-microbials.

3. The liquid enzyme formulation of claim 1, wherein:
   (a) the phytase has a concentration of 5,000 to 20,000 unit/ml,
   (b) sodium chloride at a concentration of 1% to 20% w/v,
   (c) sorbitol at a concentration of 2% to 20% w/v,
   (d) glycerol at a concentration of 2% to 40% w/v,
   (e) potassium sorbate at a concentration of 0.05% to 0.4% w/v,
   (f) sodium benzoate at a concentration of 0.05% to 0.4% w/v,
   (g) methyl paraben at a concentration of 0.05% to 0.4% w/v, or
   (g) a propionate salt at a concentration of 0.05% to 0.4% w/v, wherein the propionate salt is selected from the group consisting of calcium propionate, sodium propionate, ammonium propionate, and any combination thereof.

4. The liquid enzyme formulation of claim 3, wherein:
   (a) the phytase has a concentration of 10,000 unit/ml,
   (b) sodium chloride at a concentration of 15% w/v,
   (c) sorbitol at a concentration of 20% w/v,
   (d) glycerol at a concentration of 20% w/v,
   (e) potassium sorbate at a concentration of 0.20% w/v,
   (f) sodium benzoate at a concentration of 0.20% w/v,
   (g) methyl paraben at a concentration of 0.20% w/v, or
   (g) a propionate salt at a concentration of 0.20%, wherein the propionate salt is selected from the group consisting of calcium propionate, sodium propionate, ammonium propionate, and any combination thereof.

5. The liquid enzyme formulation of claim 1, wherein:
   (a) the phytase has a concentration of 11,000 to 12,000 unit/ml,
   (b) sodium chloride at a concentration of 15% w/v,
   (c) sorbitol at a concentration of 4% w/v,
   (d) sodium citrate at a concentration of 50 mM,
   (e) potassium sorbate at a concentration of 0.2% w/v,
   (f) sodium benzoate at a concentration of 0.1% w/v, or
   (g) sodium propionate at a concentration of 0.1%.

6. The liquid enzyme formulation of claim 5, wherein the stabilizer further comprises sorbitol at a concentration of 4% w/v and/or sucrose at a concentration of 6% w/v.

7. The liquid enzyme formulation of claim 1, wherein:
   (a) the phytase has a concentration of 44,000 to 48,000 unit/ml,
   (b) sucrose at a concentration of 20% w/v,
   (c) sodium chloride at a concentration of 1% w/v,
   (d) sodium citrate at a concentration of 50 mM,
   (e) sodium benzoate at a concentration of 0.1% w/v,
   (f) potassium sorbate at a concentration of 0.4% w/v, or
   (g) sodium propionate at a concentration of 0.4%.

8. The liquid enzyme formulation of claim 7, wherein the stabilizer further comprises sorbitol at a concentration of 2% to 40% w/v and/or sucrose at a concentration of 20% w/v.

9. The liquid enzyme formulation of claim 1, wherein said liquid enzyme formulation comprises at least two of said anti-microbials.

10. The liquid enzyme formulation of claim 1, wherein the liquid enzyme formulation is combined with an animal feed.

11. The liquid enzyme formulation of claim 10, wherein the animal feed is a dry animal feed.

* * * * *